United States Patent
Li et al.

(10) Patent No.: US 11,306,082 B2
(45) Date of Patent: Apr. 19, 2022

(54) ESTERS OF DIHYDROTETRABENAZINE

(71) Applicant: Foresee Pharmaceuticals Co., Ltd., Taipei (TW)

(72) Inventors: Yuhua Li, Landenberg, PA (US); Chen-Chang Lee, New Taipei (TW); Wen-Yen Huang, Tainan (TW)

(73) Assignee: Foresee Pharmaceuticals Co., Ltd., Taipei (TW)

( * ) Notice: Subject to any disclaimer, the term of this patent is extended or adjusted under 35 U.S.C. 154(b) by 0 days.

(21) Appl. No.: 16/762,747

(22) PCT Filed: Nov. 7, 2018

(86) PCT No.: PCT/US2018/059657
§ 371 (c)(1),
(2) Date: May 8, 2020

(87) PCT Pub. No.: WO2019/094491
PCT Pub. Date: May 16, 2019

(65) Prior Publication Data
US 2020/0270241 A1    Aug. 27, 2020

Related U.S. Application Data

(60) Provisional application No. 62/582,979, filed on Nov. 8, 2017.

(51) Int. Cl.
*C07D 455/06*    (2006.01)
*A61K 47/44*    (2017.01)

(52) U.S. Cl.
CPC ............ *C07D 455/06* (2013.01); *A61K 47/44* (2013.01); *C07B 2200/05* (2013.01)

(58) Field of Classification Search
CPC .................................................. C07D 455/06
See application file for complete search history.

(56) References Cited

U.S. PATENT DOCUMENTS

| 2008/0004342 A1 | 1/2008 | Zaloga et al. |
| 2012/0077839 A1 | 3/2012 | Gano |
| 2016/0030414 A1 | 2/2016 | Gant et al. |

FOREIGN PATENT DOCUMENTS

| WO | 03/042162 A1 | 5/2003 |
| WO | 2015171802 A1 | 11/2015 |
| WO | 2016144901 A1 | 9/2016 |
| WO | 2018178233 A1 | 10/2018 |

OTHER PUBLICATIONS

Hao, X., et al. "Pancreas-Specific Delivery of β-Cell Proliferating Small Molecules." Chem.Med.Chem. (2016), vol. 11, pp. 1129-1132. (Year: 2016).*
The International Search Report and the Written Opinion dated Jan. 7, 2019 for related PCT/US 18/59657.
International Preliminary Report on Patentability dated May 12, 2020 for related PCT/US 18/59657.
Yao et al., "Preparation and Evaluation of Tetrabenazine Enantiomers and All Eight Stereoisomers of Dihydrotetrabenazine as VMAT2 Inhibitors," European Journal of Medicinal Chemistry, Elsevier, vol. 46, No. 5, Feb. 17, 2011, pp. 1841-1848.
Skor et al., "Differences in Dihydrotetrabenazine Isomer Concentrations Following Administration of Tetrabenazine and Valbenazine," Drugs in R and D, vol. 17, No. 3, Sep. 1, 2017, pp. 449-459.
Aranda et al., "Synthesis and Biological Activity of Iodinated and Photosensitive Derivatives of Tetrabenzine," European Journal of Medicinal Chemistry, Elsevier, vol. 25, No. 4, May 1, 1990, pp. 369-374.
European Application No. 18876092.0,Extended European Search Report dated Jul. 13, 2021, 10 pages.

* cited by examiner

*Primary Examiner* — John S Kenyon
(74) *Attorney, Agent, or Firm* — MagStone Law, LLP; Enshan Hong

(57) ABSTRACT

The present invention relates to a compound of formula (I) including any stereochemically isomeric form thereof, or a pharmaceutically acceptable salt thereof.

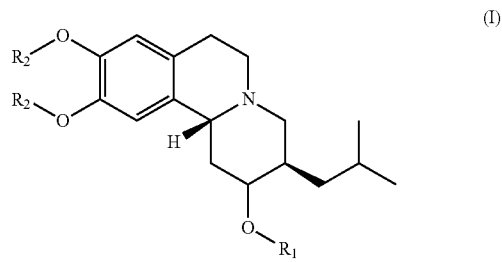

(I)

wherein $R_1$ is —C(=O)O-alkyl, carbonate ester, or —C(=O)-alkyl, ester, or —C(=O)N-alkyl, carbamate ester and wherein $R_2$ is —$CH_3$ or —$CD_3$. The alkyl ester can contain saturated or unsaturated $C_{12}$ to $C_{26}$ alkyl carbon. The alkyl carbon chain can have either a straight, branched, noncyclic, cyclic, unsubstituted or substituted structure.

14 Claims, 1 Drawing Sheet

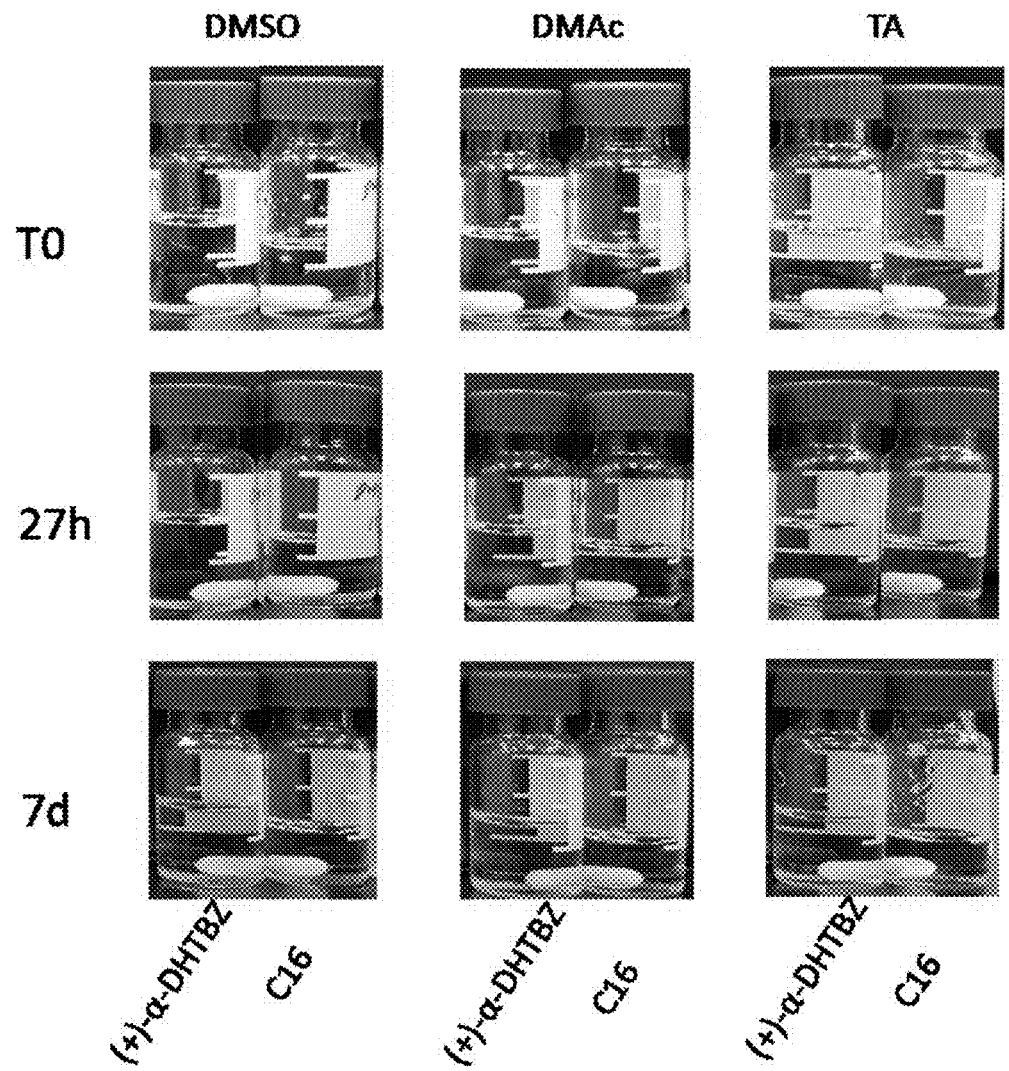
The color change of (+)-(α)-DHTBZ and (+)-(α)-DHTBZ palmitate in organic solutions at 37°C.

ESTERS OF DIHYDROTETRABENAZINE

FIELD OF THE INVENTION

The present invention relates to the compounds of formula (I), pharmaceutical compositions comprising these compounds, chemical processes for preparing these compounds and their use in the treatment of hyperkinetic diseases and disorders, such as tardive dyskinesia, by administration of such compounds to a warm-blooded animal in need thereof.

Synonyms: Dihydrotetrabenazine; DTBZ; DHTBZ
Synonyms: $d_6$-Dihydrotetrabenazine; $d_6$-DTBZ; $d_6$-DHTBZ

BACKGROUND OF THE INVENTION

The involuntary movement and repetitive body movement are typical symptoms of hyperkinetic movement disorder caused by exposure of long-term medication with dopamine amine blocking agents, such as antipsychotic agents. The actual mechanism of hyperkinetic movement disorder is still not clear. Previous data support hypothesis of upregulation and supersensitiveness of dopamine receptor, like $D_2$, resulting in chronic reduction of dopaminergic neurotransmission and causing the hyperkinetic movement disorder.

The hyperkinetic movement could start with chewing, affected normal speech, breathing, movement disorder and balance. In some severe cases, it will result in self-injury, laceration and inability for the normal life. Tardive dyskinesia (TD) is one of the family of hyperkinetic movement disorder and generally is characterized by involuntary hyperkinetic movement in orofacial area and choreoathetoid disorder in the limbs and trunk. In general, TD can be developed by long-term exposure of antipsychotic drugs and often persists even after discontinuation of treatment.

Vesicular monoamine transporter-2 (VMAT2) is a membrane protein that transports the monoamine such as dopamine, serotonin, histamine and norepinephrine from pre-synaptic into synaptic vesicle. 3-isobutyl-9,10,dimethoxy-1,3,4,6,7,11b-hexahydro-2H-pyrido[2,1-a]isoquinolin-2-one, also known as tetrabenazine (TBZ, XENAZINE®) is a potent ($IC_{50}$ is 3.2 nM, Scherman, et al., Proc. Natl. Acad. Sci. USA, 1983, 80, 584-588) and reversible VMAT2 inhibitor and has been used as treatment of hyperkinetic movement disorders, for example chorea associated with Huntington's disease and TD. However, some TBZ off-target related side effects including depression, sedation, drowsiness, dizziness, insomnia, akathisia and parkinsonism were observed and reported. Therefore, a strict RISK Evaluation and Mitigation Strategy (REMS) of XENAZINE® was issued and personalized dosing, dose titration and management of medication associated side effects are required.

TBZ is a racemic mixture and presents two chiral centers. It can be rapidly and extensively metabolized to its reduced form, 3-isobutyl-9,10-dimethoxy-1,3,4,6,7,11b-hexahydro-2H-pyrido[2,1-a]isoquinolin-2-ol, known as dihydrotetrabenzaine (DHTBZ). Due to the nature of racemic mixture, DHTBZ can be presented as four isomers, (±)-α-DHTBZ and (±)-β-DHTBZ, where the extent to which isomer can be highly variable between patients (Mehvar et al., Drug Metab. and Dispos., 1987, 15, 250-255). Among these isomers, the (+)-α-DHTBZ or 2R, 3R, 11bR-DHTBZ is considered as the major active metabolite and exhibits excellent VMAT2 binding and off-target selectivity. On the other hand, other stereoisomers present variable pharmacology effects such as weak to moderate VMAT2 binding and high affinity to some off-target receptors (Grigoriadis et al., J. Pharmacol. Exp. Ther., 2017, 361, 454-461). TBZ has been approved as hyperkinetic disorder medication; however, variable bioavailability due to the complexity of TBZ metabolism through extensive first pass effect and off-target phenomenon can result in variable inter-patient therapeutic results. Also, the short half-life and low bioavailability could cause more dosing frequency, three times per day.

The off-target effect of TBZ caused by complex racemic metabolites can result in several serious side effects, including suicidality, depression, sedation, drowsiness, dizziness, insomnia, akathisia and parkinsonism. The genotyping of individuals could exhibit different degrees of metabolism of TBZ to generate variable concentration levels of each metabolite. Also, due to the genotyping issue, the dose titration of TBZ is required.

Since the serious side effects associated with TBZ are related to the complexity of metabolism where the generated isomeric metabolites can be highly variable from patient to patient. The poor off-target selectivity of some metabolites have been shown to be responsible for these serious side effects. Therefore, the problems associated with the stereochemical metabolites can possibly be avoided by administration of the metabolite or its derivative in a single stereoisomer form.

(S)-2-amino-3-methyl-butyric acid (2R, 3R, 11bR)-3-isobutyl-9,10-dimethoxy-1,3,4,6,7,11b-hexahydro-2H-pyrido[2,1-a]isoquinolin-2-yl (Valbenazine, VBZ, INGREZZA®) described in U.S. Pat. No. 8,039,627 is a prodrug with valine substitution on the single stereoisomer (+)-(α)-DHTBZ. A prodrug is a pharmacological substance (drug) that is administered in an inactive (or significantly less active) form. Once administered, the prodrug is metabolized in vivo into its active parent drug. Administrating a prodrug of a single stereoisomer can provide the merit by avoiding exposure to all stereoisomer metabolites of dihydrotetrabenazine (DHTBZ). As disclosed in U.S. Pat. No. 8,039,627, VBZ [(+)-(α)-DHTBZ conjugated with valine, an amino acid] showed VAMT2 binding affinity, Ki, of 187 nM. The VBZ is less potent than (+)-(α)-DHTBZ, but is still quite a strong inhibitor for VMAT2.

Good stability, minimal or no VMAT2 binding, and suitable hydrolysis rate to release active drug are the key parameters in development of long acting depot of DHTBZ derivative. Although some prior arts have demonstrated chemical modification on hydroxyl containing DHTBZ, the resulting properties associated with esterified compounds varied significantly and unpredictably. For example, those described in Harriott et al, Prog. Med. Chem., 2018, 57, 87-111, Aranda et al. Euro. J. Med. Chem., 1990, 25, 369-374 and Kilbourn et al. Chirality, 1997, 9, 59-62, have shown that the hydroxyl group in DHTBZ could be utilized to form different ester modifications of DHTBZ. Aranda disclosed a caproic acid ester of DHTBZ (see page 370 of Aranda, Compound No. 6) and Kilbourn disclosed an acetic acid ester of DHTBZ (see page 60 of Kilbourn, right hand column). However, these types of compounds are not suitable for use as prodrugs of DHTBZ. As disclosed in the response to the Examiner's rejection for patent application Ser. No. 11/937,445 on Apr. 1, 2011, when tested in human liver assay, no conversion of these compounds to (+)-α-DHTBZ was observed; only VBZ, a valine modified DHTBZ, can release the active (+)-α-DHTBZ. It appears that modification with short chain (C2 and C6) aliphatic carboxylic acid would make liberation of active parent drug inefficient. Thus, neither of these prior art compounds would function as a substitute for (+)-α-DHTBZ since administration of the same fails to generate the active metabolite.

Aranda reports a VMAT2 binding affinity (EC50) for the caproic acid ester of 8.1±3.3 nM compared to 6.7±1.1 nM for (+)-(α)-DHTBZ (see Table 1, page 370). This corresponds to a Ki of 5.7 nM for the caproic acid ester compared to 4.7 nM for (+)-(α)-DHTBZ (see 16 of the Declaration). The acetate ester of Kilbourn was found to have a Ki of 16 nM compared to 5.3 nM for (+)-(α)-DHTBZ (see 17 of the Declaration). The acetate ester of Kilbourn (C2) showed lower affinity than the caproic acid ester of Aranda (C6), i.e., 16 nM vs 5.7 nM. It appears that the longer the carbon chain of the esters, the stronger the inhibitor for VAMT2. Both caproic acid ester and acetate esters are potent VAMT2 inhibitors with comparable potency (Ki) to that of (+)-(α)-DHTBZ. Therefore, these esters disclosed in Kilbourn (C2) and Aranda (C6) are not suitable for use as prodrugs. It also seems that increasing carbon chain length of the (+)-(α)-DHTBZ esters from C2 to C6 would not lead to a lower potency for VMAT2.

Although the VBZ is a successful oral dosage form, it has to be taken daily for a long time. It's still relative potent to VMAT2 receptor and not ideal for use as a prodrug. Therefore there is still a need for a much longer acting dosage form which can significantly reduce dosing frequency and improved compliance. There is also a need for a modified drug to have a lower potency to VMAT2 than VBZ.

SUMMARY OF THE INVENTION

The present invention relates to a compound of formula (I) including any stereochemically isomeric form thereof, or a pharmaceutically acceptable salt thereof.

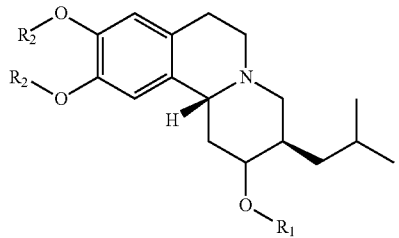

(I)

wherein $R_1$ is —C(=O)O-alkyl, carbonate ester, or —C(=O)-alkyl, ester, or —C(=O)N-alkyl, carbamate ester and wherein $R_2$ is —$CH_3$ or —$CD_3$. The alkyl ester can contain saturated or unsaturated $C_{12}$ to $C_{26}$ alkyl carbon. The alkyl carbon chain can have either a straight, branched, noncyclic, cyclic or substituted structure.

Specifically, the present invention provides the conjugations of (2R, 3R, 11bR)-3-isobutyl-9,10-dimethoxy-1,3,4,6,7,11b-hexahydro-2H-pyrido[2,1-a]isoquinolin-2-ol ((+)-α-DHTBZ) and (2S, 3R, 11bR)-3-isobutyl-9,10-dimethoxy-1,3,4,6,7,11b-hexahydro-2H-pyrido[2,1-a]isoquinolin-2-ol ((+)-β-DHTBZ) compounds, as well as the modification method of these compounds, use, and pharmaceutical compositions containing the same.

The compounds of formula (I) of the present invention has both good chemical and physical stability, minimal or no VMAT2 binding and acceptable ester hydrolysis rate.

The compounds of formula (I) of the present invention can achieve a broad spectrum of therapeutic applications, and may be used as the inhibitor for vesicular monoamine transporter 2 (VMAT2) receptor and its associated disease, such as the family of hyperkinetic movement disorder diseases.

The compounds of formula (I) of the present invention are designed to deliver the active DHTBZ in a controlled manner with less variable plasma concentration and pharmacokinetics (PK) profile, which can limit the off-target effect to provide an improved safety profile to patients. In addition, the formula (I) is the alkyl esterification of (+)-DHTBZ ((+)-α-DHTBZ) and (+)-(β-DHTBZ)), where the alkyl esterification containing $C_{12}$ to $C_{26}$ alkyl ester. The present invention provides method for the conjugation of (+)-DHTBZ with fatty acid by reacting the hydroxyl group in (+)-DHTBZ with carboxyl group in fatty acid moiety. The compounds of formula (I) of the present invention provide low aqueous solubility (e.g., less than 100 mcg/mL), suitable VMAT2 inhibition (K more than 100 nM). The compounds of formula (I) of the present invention can be administrated to a subject in need and the active DHTBZ is released after hydrolysis of the conjugate within tissue environment. The hydrolysis can be conducted via enzymatic or chemical pathway or in the combination of both pathways.

The present invention provides pharmaceutical compositions comprising at least one pharmaceutically acceptable carrier and a therapeutically effective amount of a compound of formula (I).

BRIEF DESCRIPTION OF THE FIGURES

FIG. 1: The color change of (+)-(α)-DHTBZ and (+)-(α)-DHTBZ palmitate in organic solutions at 37° C.

DETAILED DESCRIPTION OF THE INVENTION

The present invention relates to a compound of formula (I) including any stereochemically isomeric form thereof, or a pharmaceutically acceptable salt thereof.

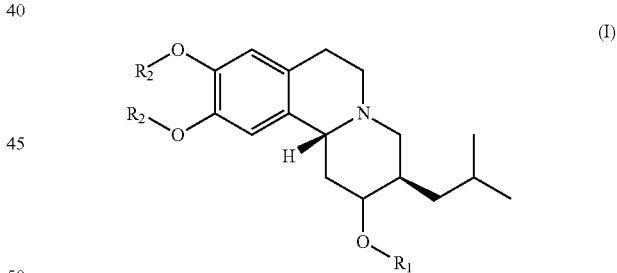

(I)

wherein $R_1$ is —C(=O)O-alkyl, carbonate ester, or —C(=O)-alkyl, ester, or —C(=O)N-alkyl, carbamate ester and wherein $R_2$ is —$CH_3$ or —$CD_3$.

As used herein, "Alkyl" means a straight chain or branched, noncyclic or cyclic, substituted, unsaturated or saturated aliphatic hydrocarbon containing from 12 to 26 carbon atoms.

As used herein, "Alkyl derivatives" includes —C(=O)O-alkyl, carbonate ester, or —C(=O)-alkyl, ester, or —C(=O)N-alkyl, carbamate ester.

The term "stereochemically isomeric forms" as used herein includes all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration. Stereochemically isomeric forms of the compounds of formula (I) are obviously intended to be embraced within the scope of this invention.

The absolute stereochemical configuration of the compounds of formula (I) and of the intermediates used in their preparation may easily be determined by those skilled in the art while using well-known methods such as, for example, X-ray diffraction.

Following abbreviations are defined as herein: TBZ-Tetrabenazine; DHTBZ-Dihydrotetrabenazine; VBZ-Valbenazine Tetrabenazine (TBZ) is a racemic mixture of (+)-TBZ (R,R-TBZ) and (−)-TBZ (S,S-TBZ) with the following structures:

(+)-TBZ (3R, 11bR-TBZ) (3R, 11bR)-3-isobutyl-9, 10,dimethoxy-1,3,4,6,7,11b-hexahydro-2H-pyrido[2,1-a]isoquinolin-2-one

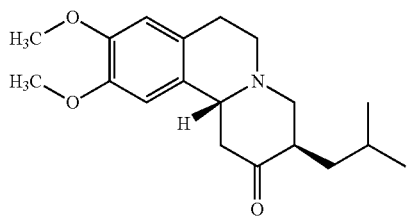
(II)

(−)-TBZ (3S,11bS-TBZ) (3S, 11bS)-3-isobutyl-9,10,dimethoxy-1,3,4,6,7,11b-hexahydro-2H-pyrido[2,1-a]isoquinolin-2-one

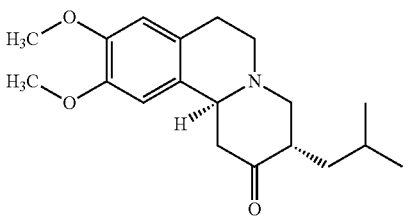
(III)

Dihydrotetrabenazine (DHTBZ) has 4 enantiomers with the following structures:

(+)-(α)-DHTBZ (2R, 3R, 11bR-DHTBZ) ((2R, 3R, 11bR)-3-isobutyl-9,10-dimethoxy-1,3,4,6,7,11b-hexahydro-2H-pyrido[2,1-a]isoquinolin-2-ol)

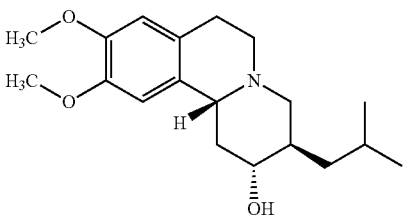
(IV)

(+)-(β)-DHTBZ (2S, 3R, 11bR-DHTBZ) ((2S, 3R, 11bR)-3-isobutyl-9,10-dimethoxy-1,3,4,6,7,11b-hexahydro-2H-pyrido[2,1-a]isoquinolin-2-ol)

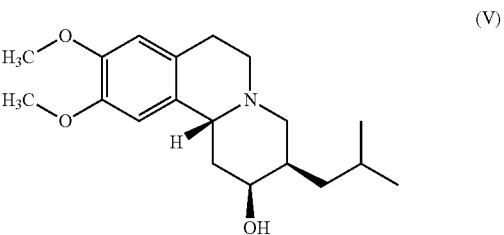 [SMILES: COc1cc2c(cc1OC)[C@H]1C[C@H](O)[C@H](CC(C)C)CN1CC2]
(V)

(−)-(α)-DHTBZ (2S,3S,11bS-DHTBZ) ((2S, 3S, 11bS)-3-isobutyl-9,10-dimethoxy-1,3,4,6,7,11b-hexahydro-2H-pyrido[2,1-a]isoquinolin-2-ol)

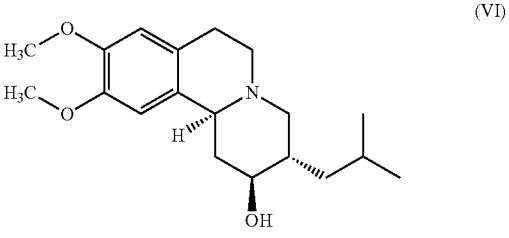 [SMILES: COc1cc2c(cc1OC)[C@@H]1C[C@H](O)[C@@H](CC(C)C)CN1CC2]
(VI)

(−)-(β)-DHTBZ (2R,3S,11bS-DHTBZ) ((2R, 3S, 11bS)-3-isobutyl-9,10-dimethoxy-1,3,4,6,7,11b-hexahydro-2H-pyrido[2,1-a]isoquinolin-2-ol)

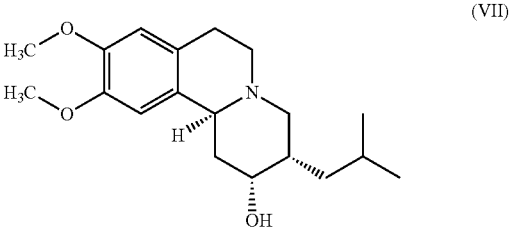 [SMILES: COc1cc2c(cc1OC)[C@@H]1C[C@@H](O)[C@@H](CC(C)C)CN1CC2]
(VII)

Valbenazine (VBZ) or R,R,R-DHTBZ-Val or [(+)-(α)-DHTBZ)]-Val (VBZ) has the following structure.

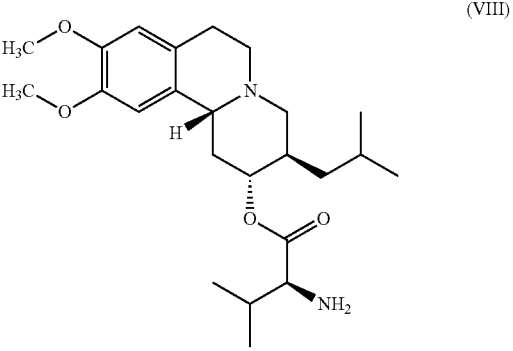 [SMILES: COc1cc2c(cc1OC)[C@H]1C[C@@H](OC(=O)[C@@H](N)C(C)C)[C@H](CC(C)C)CN1CC2]
(VIII)

(+)-(α)-DHTBZ and (+)-(β)-DHTBZ as well as their deuterated derivatives $d_6$-(+)-(α)-DHTBZ and $d_6$-(+)-(β)-DHTBZ are preferably used in the present invention to synthesize conjugates of formula (I).

The pharmaceutically acceptable salts as mentioned herein above are meant to comprise the therapeutically active non-toxic acid addition salts that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic acids and the like.

Conversely said salt forms can be converted by treatment with an appropriate base into the free base form.

In an embodiment, the present invention relates to compounds of formula (I) wherein $R_1$ is ester or carbamate ester or carbonate ester of C12-26 alkyl and $R_2$ is —$CH_3$.

In another embodiment, the present invention relates to compounds of formula (I) wherein $R_1$ is ester or carbamate ester or carbonate ester of C12-26alkyl and $R_2$ is —$CD_3$.

In another embodiment, the present invention relates to compounds of formula (I) wherein $R_1$ is derived from one of the group of lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, and cerotic acid.

In another embodiment, the present invention relates to compound of formula (I) wherein $R_1$ is ester of C16alkyl or palmitate.

In another embodiment, the present invention relates to compound of formula (I) wherein $R_1$ is ester of C18alkyl or stearate.

In another embodiment, the present invention relates to compound of formula (I) wherein $R_1$ is ester of C22alkyl or behenate.

In another embodiment, the present invention relates to compound of formula (I) wherein $R_1$ is ester of unsaturated C18alkyl or oleate.

In another embodiment, compounds of formula (Ia), defined as compounds of formula (I) wherein $R_1$ represents ester of C12-26alkyl, $R_2$ represents —$CH_3$, can be prepared by known esterification methods by reacting (+)-(α)-DHTBZ (IV) with a fatty acid of formula (IX) in the presence of 1-ethyl-3-(3-dimethylaminopropyl)carbodiimide (EDC) and 4-dimethylaminopyridine (DMAP) as a coupling reagent and a catalyst, respectively. The R substituent in the fatty acid of formula (IX) is defined as C11-25alkyl.

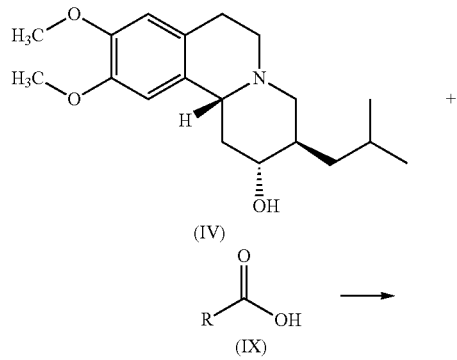

(IV)

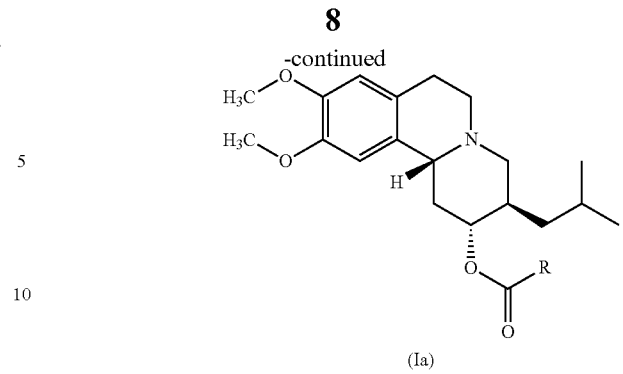

(Ia)

In another embodiment, compounds of formula (Ib), defined as compounds of formula (I) wherein $R_1$ represents ester of C12-26alkyl, $R_2$ represents —$CD_3$, can be prepared by known esterification methods by reacting $d_6$-(+)-(α)-DHTBZ (X) with a fatty acid of formula (IX) in the presence of EDC and DMAP as a coupling reagent and a catalyst, respectively. The R substituent in the fatty acid of formula (IX) is defined as C11-25alkyl.

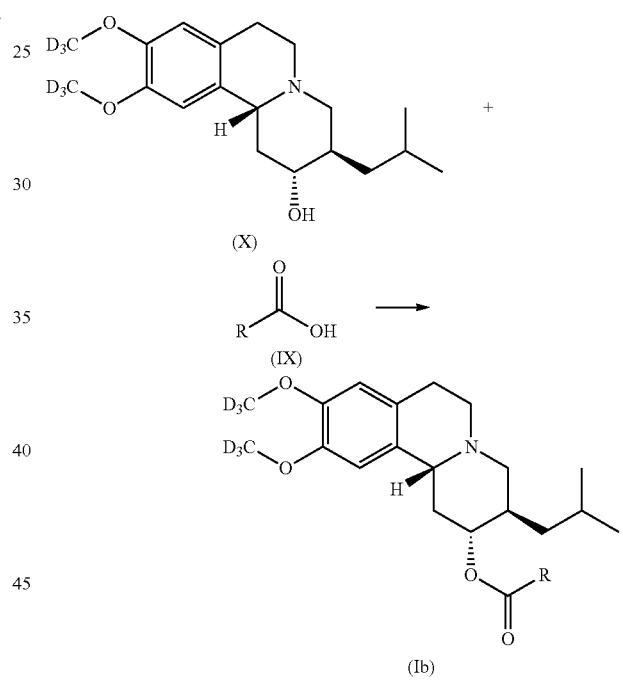

(Ib)

Alternatively, the compounds (Ia) and (Ib) can be prepared by reacting of (+)-(α)-DHTBZ (IV) and $d_6$-(+)-(α)-DHTBZ (X) with an acyl chloride of formula (XI) in the presence of a base to neutralize the acid liberated during the reaction. The R substituent in the acyl chloride of formula (XI) is defined as C11-25alkyl.

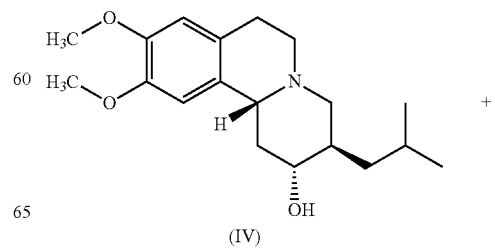

(IV)

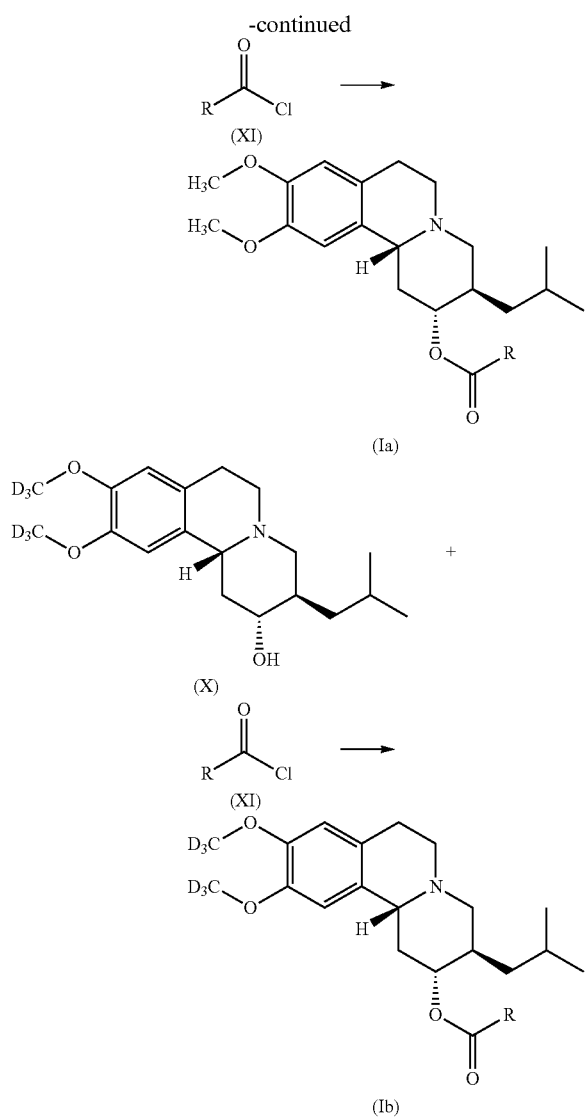

In general, the synthesis of a conjugate of this invention typically consists of the following steps:

Activation of the carboxylic group, if not already in activated form.

Addition of activated fatty acid to DHTBZ or vice versa in the presence of base

For example, to a solution of (+)-(α)-DHTBZ free base in anhydrous THF or dichloromethane (DCM) was added triethylamine (TEA). The solution was stirred and the fatty acid chloride was added drop wise at room temperature. After 2-6 hours, depending on the fatty acid derivative, solvents were evaporated to dryness and the residue was dissolved in ethyl acetate (EA). The organic phase was washed with aqueous $NaHCO_3$ and brine, dried over anhydrous $Na_2SO_4$ and evaporated to dryness to yield the fatty acid-(+)-(α)-DHTBZ conjugate.

The conjugate was converted to its hydrochloride salt by stirring with 4N HCl in dioxane for 15 min. at room temperature and evaporating the solvent to dryness. The residue was triturated with isopropanol (IPA) and the precipitate was filtered and dried to yield the hydrochloride salt of the fatty acid-(+)-(α)-DHTBZ conjugate. Similarly, other conjugates of the present application can be prepared with or without any modification of the conjugation synthesis procedure.

In another embodiment, the compounds of formula (I) show lower solubility in aqueous solution than the unconjugated compound. This is in contrast to the valbenazine (VBZ) which is a conjugate of (+)-α-DHTBZ with valine. Amino acids have been typically used to increase drug's aqueous solubility (see Jornada et al., Molecules 2016, 21, 42). This low solubility of the compounds of formula (I) may be used advantageously to develop a slow release formulations to reduce dosing frequency.

In another embodiment, the compounds of formula (I) show improved stability in organic solution. When dissolved in pharmaceutically acceptable organic solvents, the unconjugated DHTBZ will change color over time. It's unexpectedly found that when the conjugated DHTBZ is dissolved in the same solvent, the color change can be minimized or prevented. This color stabilization will be useful to develop a high quality product. The solvents disclosed herein including dimethylacetamide (DMAc), Dimethyl sulfoxide (DMSO), triacetin (TA), benzyl alcohol, benzyl benzoate, ethanol, N-methylpyrrolidone (NMP), polyethylene glycol, and the like.

In another embodiment, the compounds of formula (I) show no or minimal inhibition of VMAT2 receptor. In comparison, the VMAT2 inhibition IC50 of the compound of formula (I) is more than 200 fold than that of unconjugated parent compound as determined using radioligand binding assays. Preferably, the VMAT2 inhibition IC50 of the compound of formula (I) is more than 500 fold than that of unconjugated parent compound as determined using radioligand binding assays. More preferably, the VMAT2 inhibition IC50 of the compound of formula (I) is more than 1000 fold than that of unconjugated parent compound as determined using radioligand binding assays.

The compounds of the present invention show the advantage of being a long acting reversible inhibitor of catecholamine uptake by vesicular monoamine transporter 2 (VMAT2) for use in the treatment of hyperkinetic diseases and disorders, such as tardive dyskinesia, by administration of such compounds to a warm-blooded animal in need thereof. The compounds of formula (I) of the present invention can stably and continuously liberate free VMAT2 inhibitor within a therapeutic concentration range with a stable PK profile over a long period of time, preferably over 2 weeks and more preferably over 1 month. This can be evidenced, for example, by measuring the plasma levels after administration to an animal.

The present invention provides pharmaceutical compositions comprising at least one pharmaceutically acceptable carrier and a therapeutically effective amount of a compound of formula (I).

In order to prepare the pharmaceutical compositions of this invention, an effective amount of the particular compound, in free base or acid addition salt form, as the active ingredient is combined in intimate admixture with at least one pharmaceutically acceptable carrier, which may take a wide variety of forms depending on the form of preparation desired for administration. These pharmaceutical compositions are desirably in unitary dosage form suitable, preferably, for oral administration, rectal administration, percutaneous administration or parenteral injection.

For example, in preparing the compositions in oral dosage form, any of the usual liquid pharmaceutical carriers may be employed, such as water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve property of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives, which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof The compounds of formula (I) may be formulated for parenteral administration by injection. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The compounds of formula (I) may also be formulated in rectal compositions such as suppositories or retention enemas, e.g. containing conventional suppository bases such as cocoa butter and/or other glycerides.

Accordingly, the present invention provides the method for treatment of movement disorder associated to the VMAT2 receptor, such as tardive dyskinesia and chorea associated to Huntington's disease. The method contains a pharmaceutical composition comprising a compound of formula (I) of present invention, a VMAT2 inhibitor, and pharmaceutical acceptable carriers or diluents to have oral or parenteral administration.

EXAMPLES

HPLC Methods for analyzing the samples
Analytical HPLC Method 1
Platform: Shimadzu Nexera X2 series: equipped with an auto-sampler, an UV detector (214 nm and 254 nm)
Column: GL SCIENCES InertSustain Phenyl Gradient:
Mobile phase A-8.5 mM ammonium acetate solution (pH6.8)
Mobile phase B-ACN+3.5% THF
0-3 min 30% B,
3-10 min 30%-50% B,
10-40.5 min 50-90% B,
40.5-50 min 90% B,
50-50.5 min 90-30% B,
50.5-60 min 30% B
Flow rate: 1 mL/min
Oven temperature: 50° C.
Analytical HPLC Method 2
Platform: Shimadzu Nexera X2 series: equipped with an auto-sampler, an UV detector (214 nm and 254 nm)
Column: GL SCIENCES InertSustain Phenyl Gradient:
Mobile phase A-8.5 mM ammonium acetate solution (pH6.8)
Mobile phase B-ACN+3.5% THF
0-3 min 50%-75% B,
3-3.5 min 75% B,
3.5-3.6 m in 75-50% B,
3.6-6 min 50% B,
Flow rate: 2 mL/min
Oven temperature: 50° C.
Analytical HPLC Method 3
Platform: Shimadzu Nexera X2 series: equipped with an auto-sampler, an UV detector (214 nm and 254 nm)
Column: GL SCIENCES InertSustain Phenyl Gradient:
Mobile phase A-8.5 mM ammonium acetate solution (pH6.8)
Mobile phase B-ACN+3.5% THF
0-2 min 80%-95% B,
2-4 min 95% B,
4-4.1 min 95-80% B,
4.1-7 min 80% B,
Flow rate: 2 mL/min
Oven temperature: 50° C.
Analytical HPLC Method 4
Platform: Shimadzu Nexera X2 series: equipped with an auto-sampler, an UV detector (214 nm and 254 nm)
Column: GL SCIENCES InertSustain Phenyl Gradient:
Mobile phase A-8.5 mM ammonium acetate solution (pH6.8)
Mobile phase B-ACN+3.5% THF
0-2 min 80%-95% B,
2-5 min 95% B,
5-5.1 min 95-80% B,
5.1-8 min 80% B,
Flow rate: 2.5 mL/min
Oven temperature: 50° C.

Example 1

(2R,3R, 11bR)-3-isobutyl-9,10-dimethoxy-1,3,4,6,7,11b-hexahydro-2H-pyrido[2,1-a]isoquinolin-2-yl palmitate (compound 1-1)

Palmitic acid (120.4 mg, 0.47 mmol) and 4-dimethylaminopyridine (DMAP) (15.3 mg, 0.12 mmol) were dissolved in anhydrous $CH_2C_{12}$ (2 mL) and 1-Ethyl-3-(3-dimethylanopropyl)carbodiimide (EDC) (110.8 uL, 0.62 mmol) was added to the previous solution under an inert environment. The mixture was stirred at room temperature for 5-10 min. The (2R, 3R, 11bR)-3-isobutyl-9,10-dimethoxy-1,3,4,6,7,11b-hexahydro-2H-pyrido[2,1-a]isoquinolin-2-ol (100 mg, 0.31 mmol) dissolved in anhydrous $CH_2Cl_2$ (2 mL) was subsequently added to the previous mixture under an inert environment. The reaction mixture was stirred at room temperature overnight and then concentrated. The purification of resulted compound was via flash column chromatography ($R_f$=0.15 at EA/Hex=⅕) and gave 105.9 mg of compound 1-1 in 61% yield. NMR (400 MHz, CDCl$_3$): 0.83-0.89 (m, 9H), 0.97-1.04 (m, 1H), 1.22-1.41 (m, 24H), 1.44-1.49 (dd, 1H), 1.59-1.67 (m, 4H), 1.93-2.07 (m, 2H), 2.30-2.34 (m, 2H), 2.43-2.63 (m, 3H), 2.95-3.16 (m, 2H), 3.18 (d, 1H), 3.82 (s, 6H), 4.62-4.66 (m, 1H), 6.55 (s, 1H), 6.60 (s, 1H). ESI-MS [M+H] calcd: 558.4; Found: 558.5.

Example 2

(2R,3R, 11bR)-3-isobutyl-9,10-dimethoxy-1,3,4,6,7, 11b-hexahydro-2H-pyrido[2,1 a]isoquinolin-2-yl behenate (compound 1-2)

Behenic acid (240.1 mg, 0.71 mmol) and 4-dimethylaminopyridine (DMAP) (22.9 mg, 0.19 mmol) were dissolved in the mixture of anhydrous CH$_2$Cl$_2$ (4 mL) and THF (2 mL) and 1-Ethyl-3-(3-dimethylaminopropyl)carbodiimide (EDC) (166.4 uL, 0.94 mmol) was added to the previous solution under an inert environment. The mixture was stirred at room temperature for 5-10 min. The (2R,3R,11bR)-3-isobutyl-9,10-dimethoxy-1,3,4,6,7,11b-hexahydro-2H-pyrido[2,1-a]isoquinolin-2-ol (150 mg, 0.47 mmol) dissolved in anhydrous CH$_2$Cl$_2$ (2 mL) was subsequently added to the previous mixture under an inert environment. The reaction mixture was stirred at room temperature overnight and then concentrated. The purification of resulted compound was via flash column chromatography ($R_f$=0.15 at EA/Hex=⅕) and gave 116 mg of compound 1-2 in 39% yield. NMR (400 MHz, CDCl$_3$): 0.84-0.90 (m, 9H), 0.98-1.04 (m, 1H), 1.23-1.41 (m, 36H), 1.44-1.49 (dd, 1H), 1.60-1.66 (m, 4H), 1.93-2.08 (m, 2H), 2.30-2.34 (m, 2H), 2.44-2.63 (m, 3H), 2.95-3.16 (m, 2H), 3.19 (d, 1H), 3.82 (s, 6H), 4.61-4.66 (m, 1H), 6.55 (s, 1H), 6.60 (s, 1H). ESI-MS [M+H] calcd: 642.5; Found [M+H]: 642.5.

Example 3

(2R,3R, 11bR)-3-isobutyl-9,10-dimethoxy-1,3,4,6,7, 11b-hexahydro-2H-pyrido[2,1 a]isoquinolin-2-yl stearate (compound 1-3)

Stearic acid (133.4 mg, 0.47 mmol) and 4-dimethylaminopyridine (DMAP) (7.7 mg, 0.06 mmol) were dissolved in anhydrous CH$_2$Cl$_2$ (4 mL) and 1-Ethyl-3-(3-dimethylaminopropyl)carbothimide (EDC) (110.8 uL, 0.62 mmol) was added to the previous solution under an inert environment. The mixture was stirred at room temperature for 5-10 min. The (2R, 3R, 11bR)-3-isobutyl-9,10-dimethoxy-1,3,4,6,7, 11b-hexahydro-2H-pyrido[2,1-a]isoquinolin-2-ol (100 mg, 0.31 mmol) dissolved in anhydrous CH$_2$Cl$_2$ (2 mL) was subsequently added to the previous mixture under an inert environment. The reaction mixture was stirred at room temperature overnight and then concentrated. The purification of resulted compound was via flash column chromatography ($R_f$=0.15 at EA/Hex=⅕) and gave 100.3 mg of compound 1-3 in 55% yield. NMR (400 MHz, CDCl$_3$): 0.83-0.90 (m, 9H), 0.96-1.04 (m, 1H), 1.20-1.40 (m, 28H), 1.43-1.48 (dd, 1H), 1.58-1.70 (m, 4H), 1.92-2.10 (m, 2H), 2.32-2.36 (m, 2H), 2.49-2.63 (m, 3H), 2.94-3.12 (m, 2H), 3.17 (d, 1H), 3.82 (s, 6H), 4.61-4.67 (m, 1H), 6.55 (s, 1H), 6.60 (s, 1H). ESI-MS [M+H] calcd: 586.5; Found [M+H]: 586.5.

Example 4

(2R,3R, 11bR)-3-isobutyl-9,10-dimethoxy-1,3,4,6,7, 11b-hexahydro-2H-pyrido[2,1 a]isoquinolin-2-yl laurate (compound 1-4)

Lauric acid (141.2.4 mg, 0.71 mmol) and 4-dimethylaminopyridine (DMAP) (22.9 mg, 0.19 mmol) were dissolved in anhydrous CH$_2$Cl$_2$ (6 mL) and 1-Ethyl-3-(3-dimethylaminopropyl)carbodiimide (EDC) (166.4 uL, 0.94 mmol) was added to the previous solution under an inert environment. The mixture was stirred at room temperature for 5-10 min. The (2R, 3R, 11bR)-3-isobutyl-9,10-dimethoxy-1,3,4,6,7, 11b-hexahydro-2H-pyrido[2,1-a]isoquinolin-2-ol (150 mg, 0.47 mmol) dissolved in anhydrous CH$_2$Cl$_2$ (2 mL) was subsequently added to the previous mixture under an inert environment. The reaction mixture was stirred at room temperature overnight and then concentrated. The purification of resulted compound was via flash column chromatography ($R_f$=0.15 at EA/Hex=⅕) and gave 113.7 mg of compound 1-4 in 48% yield. NMR (400 MHz, CDCl$_3$): 0.83-0.90 (m, 9H), 0.98-1.04 (m, 1H), 1.21-1.41 (m, 16H), 1.41-1.49 (dd, 1H), 1.59-1.66 (m, 4H), 1.93-2.08 (m, 2H), 2.32-2.38 (m, 2H), 2.43-2.63 (m, 3H), 2.95-3.12 (m, 2H), 3.17 (d, 1H), 3.81 (s, 6H), 4.62-4.65 (m, 1H), 6.55 (s, 1H), 6.60 (s, 1H). ESI-MS [M+H] calcd: 502.4; Found [M+H]: 502.4.

Example 5

Aqueous Solubility of Various Compounds

Compound suspensions (2 mg/m L) in various aqueous solutions, including 10 mM pH 4.0 citrate-saline buffer, 10 mM pH 5.0 citrate-saline buffer, 10 mM pH 5.8 PBS, 10 mM pH 7.4 PBS, 10 mM pH 8.5 borate-saline buffer, pure water and serum, were stirred at 37° C. for 2-3 days. Daily, 0.5 to 1 mL aliquots were taken and centrifuged at 14,000 rpm for 2 min without temperature control. The supernatant was analyzed by HPLC to determine the amount of dissolved compounds. Table 1 shows the solubility of the compound 1-1, 1-2 and compound IV in various aqueous solutions. Compound 1-1 and 1-2 present significantly lower aqueous solubility than compound IV in all tested conditions.

TABLE 1

Aqueous solubility of compounds

| Medium | Solubility (mcg/mL) | | |
|---|---|---|---|
| | Compd IV | Compd 1-1 | Compd 1-2 |
| Citrate buffer (10 mM, pH 5.0) | >2000 | BQL | BQL |
| PBS (10 mM, pH 5.8) | 1381.3 | BQL | BQL |
| PBS (10 mM, pH 7.4) | 243.6 | 1.0 | BQL |
| Borate (10 mM, pH 8.5) | 140.3 | 32.6 | 1.7 |

Note:
BQL (below quantitation limit); the quantitation limit is 1 mcg/mL.

It is interesting to note that the aqueous solubility of Compound IV decreases with the increase of pH, while the aqueous solubility of Compounds 1-1 and 1-2 increases with the increase of pH. As VBZ is an amino acid modified conjugate, the pH effect on its aqueous solubility trend is expected to be similar to that of Compound IV.

Example 6

Solubility of Compounds in Pharmaceutical Acceptable Organic Solvents

Previously, non-aqueous solvents, such as organic solvents, have long been utilized in injectable pharmaceutical products to dissolve water-insoluble drugs. Here, the solubility of compounds of the present application in various organic solvents were tested. The compound suspensions in various pharmaceutical acceptable organic solvents, including dimethylacetamide (DMAc), Dimethyl sulfoxide (DMSO), triacetin (TA), were stirred at 37° C. at designed time interval. At the designed time point, 0.5 mL aliquots were taken and centrifuged at 14,000 rpm for 2 min without temperature control. The supernatant was diluted with ACN and then analyzed by HPLC to determine the amount of dissolved compounds. Table 2 shows the solubility of compound 1-1, compound 1-2 and compound IV in different pharmaceutical acceptable organic solvents after incubation, where Compound 1-1 presents good solubility in all tested solvent, but compound 1-2 show much lower solubility of 0.15 mg/mL in DMSO and 8.81 mg/mL in DMAc. Surprisingly, the unconjugated compound IV showed significant color change over time, while the conjugated compounds 1-1 and 1-2 showed no or minimal color change after incubation at 37° C. for 7 days (FIG. 1). The conjugation as defined in compound of formula (I) significantly improves the unconjugated compound's color stability in organic solvents.

TABLE 2

Solubility of compounds in pharmaceutical acceptable organic solvents

| Incubation | Medium | Solubility (mg/mL) | | |
|---|---|---|---|---|
| | | Compd IV | Compd 1-1 | Compd 1-2 |
| 37° C. | DMSO | 409.7 | 7.8 | 0.15 |
| | DMAc | 555.4 | 512.9 | 8.81 |
| | Triacetin | 26.1 | 29.9 | N/A |

Example 7

Solubility of Compounds in Pharmaceutical Acceptable Oils

Conventionally, fatty acids are used to conjugate with a drug to enhance drug's lipophilicity to increase its solubility in oils. The solubility of compounds of the present application in various oils were tested. The suspension of compounds in various pharmaceutical acceptable oils, including castor oil, sesame oil, cottonseed oil, peanut oil and soybean oil, were stirred at 37° C. for 2-3 days. At designed time point, about 200 to 300 μL aliquots were taken and centrifuged at 14,000 rpm for 2 min without temperature control. The supernatant was carefully withdrawn and extracted with 9 folds of ACN. The mixture was then vortexed for 30 sec and subsequently centrifuged at 14,000 rpm for 2 min without temperature control. The supernatant (300 uL) was taken and diluted with 1 fold of isopropanol (IPA) and then analyzed by HPLC to determine the amount of dissolved compounds. The oil without compound after same extraction/dilution step was used as control. As shown in Table 3, all compounds 1-1, 1-2 and IV show fair to good solubility in pharmaceutical acceptable oils. The conjugation significantly increases the solubility in various oils. The higher oil solubility can be advantageously used to make long acting or sustained release formulation to deliver the active compounds.

TABLE 3

Solubility of compounds in pharmaceutical acceptable oils

| | Solubility (mg/mL) | | |
|---|---|---|---|
| Medium | Compd IV | Compd 1-1 | Compd 1-2 |
| Castor oil | 30.0 | 369.9 | 31.4 |
| Peanut oil | 10.1 | 266.5 | 70.2 |
| Soybean oil | 8.0 | 276.7 | 96.4 |

Example 8

Hydrolysis of Compound in Aqueous Solutions

The method was modified from Wang et al. J. Pharm. Sci, 2016, 105, 773-785. In short, the aqueous hydrolysis of compounds were performed in isotonic pH 7.4 PBS, 10 mM pH 4.0 citrate-saline buffer and 10 mM, pH 8.5 borate-saline buffer at 37° C. Due to the low aqueous solubility of palmitate and behanate derivatives, the derivative was firstly dissolved in ACN containing 0.1% TFA at 5 mg/mL as a stock solution. Then, 0.1 to 0.25 mL aliquot of each stock solution in 20 mL screw cap glass vial were carefully diluted with the corresponding aqueous solutions to final concentration of compounds at 0.05 mg/mL, 2.5% v/v. Beside, various concentrations of ACN containing 0.1% TFA (1% to 15%) in PBS buffer were used to examine the effect of ACN containing 0.1% TFA on the hydrolysis rate. The 10% v/v ACN containing 0.1% TFA/aqueous solution was prepared as the control. The vials were kept in dark and stirred with magnetic stirrer in the incubators. Over a period of 30 min to 48 h, a 200 to 300 μL aliquot of tested solution was withdrawn into an Eppendorf tube and stored at −20° C. till HPLC analysis. Prior HPLC analysis, the tested solution was centrifuged at 14,000 rpm for 2 min at room temperature. The supernatant of each solution was taken for the HPLC analysis.

Example 9

Enzymatic Hydrolysis of Compound 1-1

The compound solution was prepared as described in Example 8. In short, each tested condition contained 0.4 μmole of compounds in 1.5 mL Eppendorf tube. The porcine liver esterase (PLE) was dissolved in PBS (pH 7.4, 10 mM) and the final ratio of esterase to compound in the reaction container was varied from 20 to 1. Final % of ACN is 10%. The PLE solution was equilibrated at 37° C. for 1 hour before adding to the compound 1-1 solution in a 1.5 mL Eppendorf tube. After incubated for 80 min at 37° C., a 100 μL aliquot of tested solution was withdrawn into an Eppendorf tube and centrifuged at 14,000 rpm for 2 min without temperature control. The supernatant was carefully withdrawn for HPLC analysis. As shown in Table 4, compound 1-1 can be hydrolyzed at the PLE/compound ratio of 5 or above to release the active compound (+)-α-DHTBZ.

TABLE 4

Ester hydrolysis of compound 1-1 via porcine liver esterase

| PLE:compound 1-1 | Incubation Time 80 min (+)-α-DHTBZ |
|---|---|
| 1:1 | BQL |
| 5:1 | 0.22 mcg/mL |
| 20:1 | 3.84 mcg/mL |

Example 10

Vesicular Monoamine Transporter Isoform 2 (VMAT2) Binding Assay

The (+)-α-DHTBZ, compounds 1-1 and 1-2 were tested for the VMAT2 binding affinity. Methods employed in this study were adapted from the scientific literatures to maximize reliability and reproducibility (see Nickell et al., J. Pharmacol. Exp. Ther., 2011, 336, 724-733 and Teng et al., J. Neurochem., 1998, 71, 258-265). Reference standards were run as an integral part of each assay to ensure the validity of the results obtained.

$IC_{50}$ values were determined by a non-linear, least squares regression analysis using MathIQ™ (ID Business Solutions Ltd., UK). Where the Ki values were calculated using the equation of Cheng and Prusoff (see Cheng et al., Biochem. Pharmacol., 1973, 22, 3099-3108) using the observed $IC_{50}$ of the tested compound, the concentration of radioligand employed in the assay, and the historical values for the Kd of the ligand (obtained experimentally at Eurofins Panlabs Inc.).

The VMAT2 competition binding assay was performed at Eurofins Panlabs Taiwan Ltd. (Item 252020) and the condition is listed below.
Source: Whole brain (without cerebellum) membranes
Ligand: [$^3$H] Dihydrotetrabenazine, 10 nM.
Incubation condition: 30 min at 25° C.
Incubation buffer: 25 mM HEPES, 100 mM potassium tartrate, 5 mM MgSO4, 0.1 mM
EDTA and 0.05 mM EGTA, pH 7.4.
Non-specific ligand: Ro4-1284, 10 μM.
Control inhibitor: Tetrabenezine
Kd: 14 nM
Bmax: 1.6 pmole/mg protein.
Quantitation method: Scintillation counting.

In Table 5, the compound IV shows strong VMAT2 receptor binding similar to literature reported result. Surprisingly and unexpectedly, both compound 1-1 and compound 1-2 presented pretty weak VMAT2 binding affinity, having a Ki of more than 10 μM. This indicates that compound 1-1 and compound 1-2 are at least 1000-fold less potent than (+)-α-DHTBZ as VMAT2 inhibitor. This property is very desirable for using compound 1-1 and compound 1-2 as prodrugs.

TABLE 5

VMAT2 binding affinity of compounds
VMAT2 binding affinity

| Item | $IC_{50}$ (nM) | Ki (nM) |
|---|---|---|
| Compd IV | 8.17 ± 0.59 | 4.77 |
| Compd 1-1 | >10 μM | >10 μM |
| Compd 1-2 | >10 μM | >10 μM |

From the above experimental data, we find that the palmitate and behenate esters of the compound of formula (I) exhibit desirable prodrug properties of good chemical and physical stability, minimal or no VMAT2 binding and acceptable ester hydrolysis rate. It is reasonable to extrapolate from this data to various other esters of the compound of formula (I) where the alkyl derivative esters are similar to the palmitate and behenate esters, including alkyl derivative esters of the compound of formula (I) where the alkyl contains carbon atoms within the range of 16 (as in the palmitate ester) and 22 (as in the behenate ester). Further, we believe that the alkyl derivative esters of the compound of formula (I) of the present invention may exhibit desirable prodrug properties where the alkyl contains a range of 12 to 26 carbon atoms based on the similarity in their chemical structure.

What is claimed is:

1. A compound of formula (I)

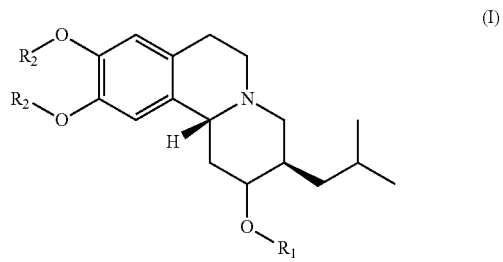

or a pharmaceutically acceptable salt thereof; wherein $R_1$ is selected from the group consisting of —C(=O)O-alkyl, —C(=O)-alkyl, and —C(=O)N-alkyl, and wherein the alkyl is a saturated or unsaturated straight-chain alkyl group containing from 11 to 25 carbon atoms, and $R_2$ is —$CH_3$ or —$CD_3$.

2. A pharmaceutical composition comprising a therapeutically effective amount of compound of claim 1 and a pharmaceutically acceptable carrier or diluent.

3. The compound as claimed in claim 1, wherein the compound has a formula of (Ia)

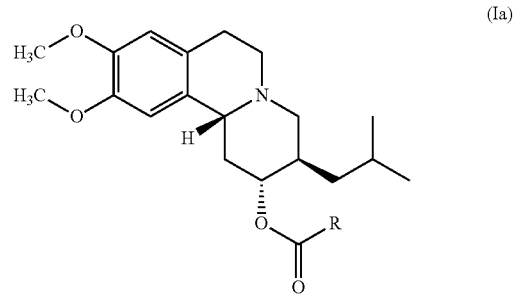

or a pharmaceutically acceptable salt thereof; wherein R is a saturated or unsaturated straight-chain alkyl group containing from 11 to 25 carbon atoms.

4. A compound of a formula of (Ib)

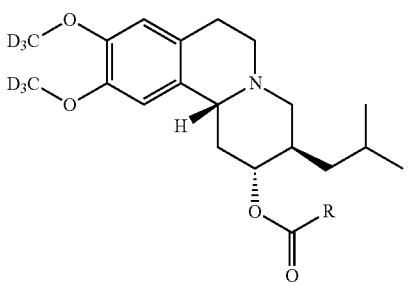

(Ib)

or a pharmaceutically acceptable salt thereof; wherein R is a saturated or unsaturated straight-chain alkyl group containing from 11 to 25 carbon atoms.

5. The compound as claimed in claim 1 wherein $R_1$ is palmitoyl.

6. The compound as claimed in claim 1 wherein $R_1$ is stearoyl.

7. The compound as claimed in claim 1 wherein $R_1$ is behenoyl.

8. The compound as claimed in claim 1 wherein $R_1$ is oleoyl.

9. The compound as claimed in claim 1 wherein the VMAT2 inhibition $IC_{50}$ of the compound is more than 200 fold than that of unconjugated parent compound as determined using Radioligand Binding Assays.

10. The compound as claimed in claim 1 wherein the VMAT2 inhibition $IC_{50}$ of the compound is more than 500 fold than that of unconjugated parent compound as determined using radioligand binding assays.

11. The compound as claimed in claim 1 wherein the VMAT2 inhibition $IC_{50}$ of the compound is more than 1000 fold than that of unconjugated parent compound as determined using radioligand binding assays.

12. The compound as claimed in claim 1, wherein the compound results in lower solubility in aqueous solution comparing with unconjugated (+)-(α)-DHTBZ.

13. The composition according to claim 2, wherein the pharmaceutical acceptable carrier is selected from the group consisting of DMSO, NMP, DMAc, benzyl alcohol (BA), benzyl benzoate (BB), ethanol, glycofurol, triacetin and glycerol.

14. The composition according to claim 2, wherein the pharmaceutical acceptable carrier is selected from the group consisting of sesame oil, vegetable oil, corn oil, soybean oil, castor oil, cottonseed oil, peanut oil and olive oil.

* * * * *